United States Patent [19]

Morris et al.

[11] Patent Number: 5,199,940
[45] Date of Patent: Apr. 6, 1993

[54] POSTURE TRAINING AND CORRECTING DEVICE

[76] Inventors: James B. Morris, 1709 Vista St., Durham, N.C. 27701; Anita M. Dale, 12758 Mulholland Dr., Beverly Hills, Calif. 90210

[21] Appl. No.: 757,972

[22] Filed: Sep. 12, 1991

[51] Int. Cl.⁵ .......................... A61F 5/00; A61G 15/00
[52] U.S. Cl. ...................................... 602/19; 128/845; 128/870; 2/44; 602/17
[58] Field of Search ................................ 602/5, 17–19; 2/44, 45; 128/845, 869–870; 606/54, 55, 241; 482/124

[56] References Cited

U.S. PATENT DOCUMENTS

| | | | |
|---|---|---|---|
| 30,601 | 11/1860 | Wright | 602/19 |
| 443,764 | 12/1890 | Hilliard | 602/19 |
| 954,005 | 4/1910 | Roth | 602/19 |
| 1,301,276 | 4/1919 | Kroetz | 602/17 X |
| 3,620,211 | 11/1971 | Goodell | 602/19 X |
| 4,007,733 | 2/1977 | Celeste et al. | |
| 4,055,168 | 10/1977 | Miller et al. | |
| 4,080,962 | 3/1978 | Berkeley | |
| 4,325,363 | 4/1982 | Berkeley | |
| 4,438,763 | 3/1984 | Zablen | 128/845 |
| 4,750,480 | 6/1988 | Jenness | |
| 5,007,413 | 4/1991 | Aalvik Thune | 602/19 X |
| 5,040,524 | 8/1991 | Votel et al. | |
| 5,086,757 | 2/1992 | Lestini | 602/19 X |

Primary Examiner—Richard J. Apley
Assistant Examiner—Linda C. M. Dvorak

[57] ABSTRACT

A postural training and correcting device comprises a rod which is held firmly to a wearer's spine by way of adjustable elastic belts around the abdominal, shoulder, and head areas and achieves correct postural alignment by encouraging the wearer to hold in the abdominal muscles, hold the upper thoracic spine upright, and keep the neck and head in correct postural alignment with the wearer's body.

4 Claims, 3 Drawing Sheets

POSTURE TRAINING AND CORRECTING DEVICE

BACKGROUND OF THE INVENTION

1. Field of the Invention

This invention relates to a posture training and correcting device, particularly to a device which corrects poor posture and encourages good posture by causing the correct postural alignment of the relevant parts of the wearer's body, and by strengthening the muscles of those body parts so that the wearer can eventually subconsciously assume correct postural alignment without the aid of the device.

2. Description of the Related Art

Correct posture involves the proper alignment of a person's pelvis, abdomen, rib cage, shoulders, neck and head relative to each other. It is sometimes difficult to pinpoint which body part is out of alignment in determining the cause of poor posture. In teaching patients about correct posture, it is common practice for doctors and postural experts to instruct patients to stand with their backs against a wall, knees bent, pressing the pelvis, spine, shoulders and back of the head against the wall. This position is said to simulate proper posture position. In aligning the parts of the body in this manner, three groups of muscles are contracted: (1) the abdominal muscles are contracted to pull in the abdomen; (2) the upper thoracic spinal muscles pull the shoulders, neck and head up and backward; and (3) the rib elevator muscles pull the ribs up and out and forward. In determining the degree and cause of poor posture, and in recommending a solution to poor posture, it is necessary to exercise control over all the body areas mentioned to ensure correct postural alignment is achieved.

Several posture correcting devices have been proposed. Various brace-type devices or corsets have been developed as posture support devices. For example, the Posture-Training Brace of Berkeley (U.S. Pat. No. 4,080,962), describes a corset-type device which is designed for the lower lumbar and lower thoracic spine. The Posture Training Therapeutic Neck Support of Berkeley (U.S. Pat. No. 4,325,363) describes a collar device which surrounds the neck for neck support. While these devices provide support to isolated areas of the relevant posture body parts, they do not provide correction or support to the upper thoracic spine or the head; nor do they provide correction or support to all relevant body parts simultaneously to achieve correct postural alignment.

Other devices similarly provide support to one isolated body part such that when that body part falls out of proper posture, a signalling device is activated to remind the wearer to regain proper posture. For example, the Posture Training Device of Miller and Dworkin (U.S. Pat. No. 4,055,168) describes a device which is worn about a person's torso by harnesses with cables such that when a change in posture or curvature of the spinal column occurs, a signal is sounded to indicate poor posture. The Posture Training Device of Celeste, Drum and Nelson (U.S. Pat. No. 4,007,733) describes an adjustable shoulder strap which attaches to a wearer's clothing and includes a signalling device which sounds if a decrease in the tension on the strap occurs. The Posture-Correcting Device of Jenness (U.S. Pat. No. 4,750,480) describes both an abdomen harness and a shoulder harness which are strapped to the wearer's body. If the wearer slouches or relaxes the abdomen muscles, a signalling device is activated to remind the wearer to maintain a good posture. The difficulty with the signalling devices is that false signals often occur, for example, when the wearer breathes or changes position in the course of normal activity. These devices are highly technical and confusing to the user.

Only one portion of the relevant body parts is isolated by the devices described above. None of these devices makes the wearer completely conscious of the total postural complex of the pelvis, abdomen, upper thoracic spine, chest, neck and head. Additionally, none of these devices has the ability to demonstrate to those observing the wearer the correct as well as the correct postural alignment of all the relevant body parts.

It is therefore an object of this invention to provide a posture training and correcting device which creates for the wearer a correct postural alignment and illustrates to observers the improper alignment and the aspired to proper alignment.

It is a further object of this invention to provide a posture training and correcting device which is not adversely affected by the normal movements or functions of the wearer.

A further object of this invention is to provide a posture training and correcting device which will cause the wearer to strengthen his or her own muscles and subconsciously assume the correct postural alignment.

It is a further object of this invention to provide a posture training and correcting device which is easy and unobtrusive to use so as to ensure use by the wearer.

Other objects and advantages will be more fully apparent from the following disclosure and appended claims.

SUMMARY OF THE INVENTION

The posture training and correcting device of the invention comprises a semi-rigid or substantially rigid lightweight rod which fits against the spine of a wearer. The rod with lower end tapered is centered from the base of the spine upward over the lumbar and thoracic cervical area of the spine, ending at the top of the head. The rod is held securely against the spine by two elastic belts, one at the lumbar section of the wearer and a second at the head across the forehead. The straps are mounted so as to be adjustable axially and are also adjustable lengthwise to accommodate different body widths or configurations. The manner in which the posture training and correcting device is designed permits the wearer to continue with his or her normal activities. An alternative embodiment incorporates the use of an elastic shoulder strap.

While using the device, the muscles of the wearer contract to relieve the pull of the elastic belts. The contraction of the wearer's muscles used to press the spine and head against the rod corresponds to a person pressing the spine against a wall. Experts agree this action causes (1) the abdominal muscles to contract, (2) the rib elevator muscles to pull the ribs up and out in front, and (3) the upper thoracic muscles to pull the shoulders, neck and head up and backward. After continued use of the device, the wearer will subconsciously contract those muscles, thus providing a method of training the body to achieve a correct postural alignment while standing, walking or sitting.

Other aspects and features of the invention will be more fully apparent from the following disclosure and appended claims.

DETAILED DESCRIPTION OF THE INVENTION AND PREFERRED EMBODIMENTS THEREOF

Figure 1:
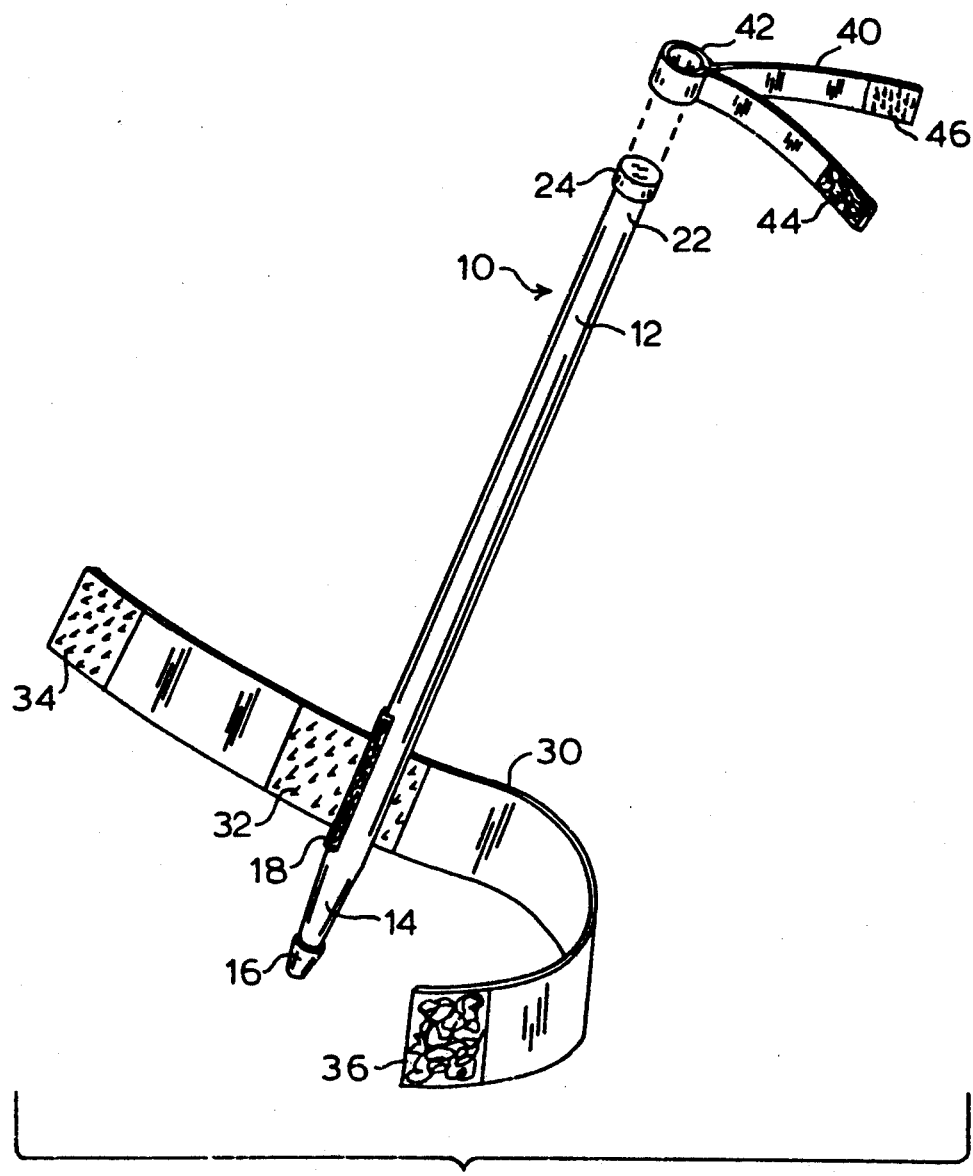
FIG. 1 is an exploded view of the posture training and correcting device of the invention according to a first embodiment.
Figure 2:
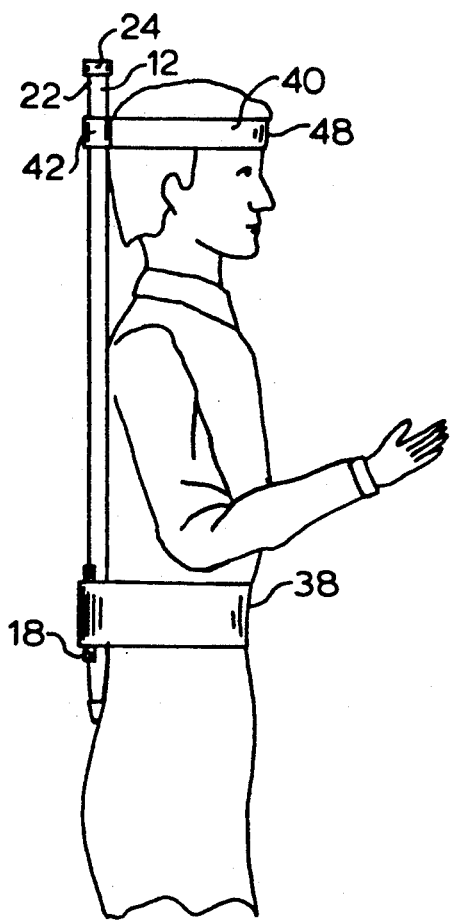
FIG. 2 is a side view of a wearer utilizing the assembled device of FIG. 1.
Figure 4:
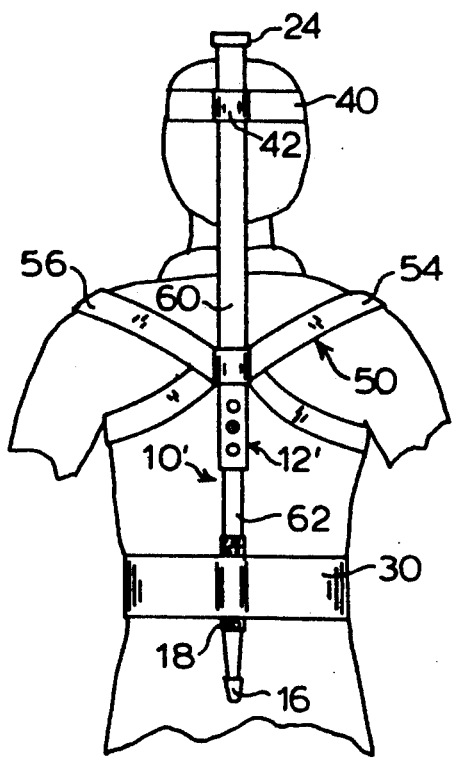
FIG. 4 is a back view of a wearer utilizing the assembled device of FIG. 3.
Figure 5:
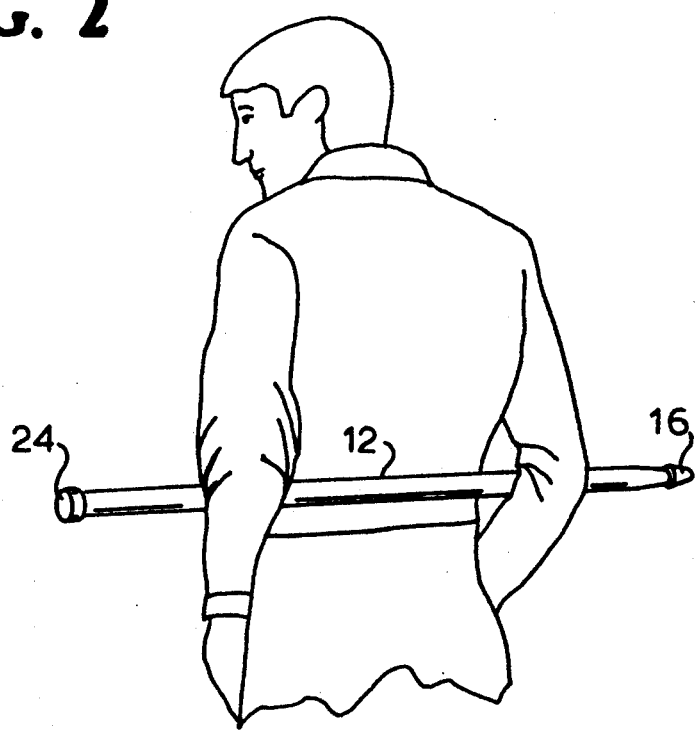
FIG. 5 is a side view of a wearer illustrating an alternate use of the rod of the posture training and correcting device.
Figure 3:
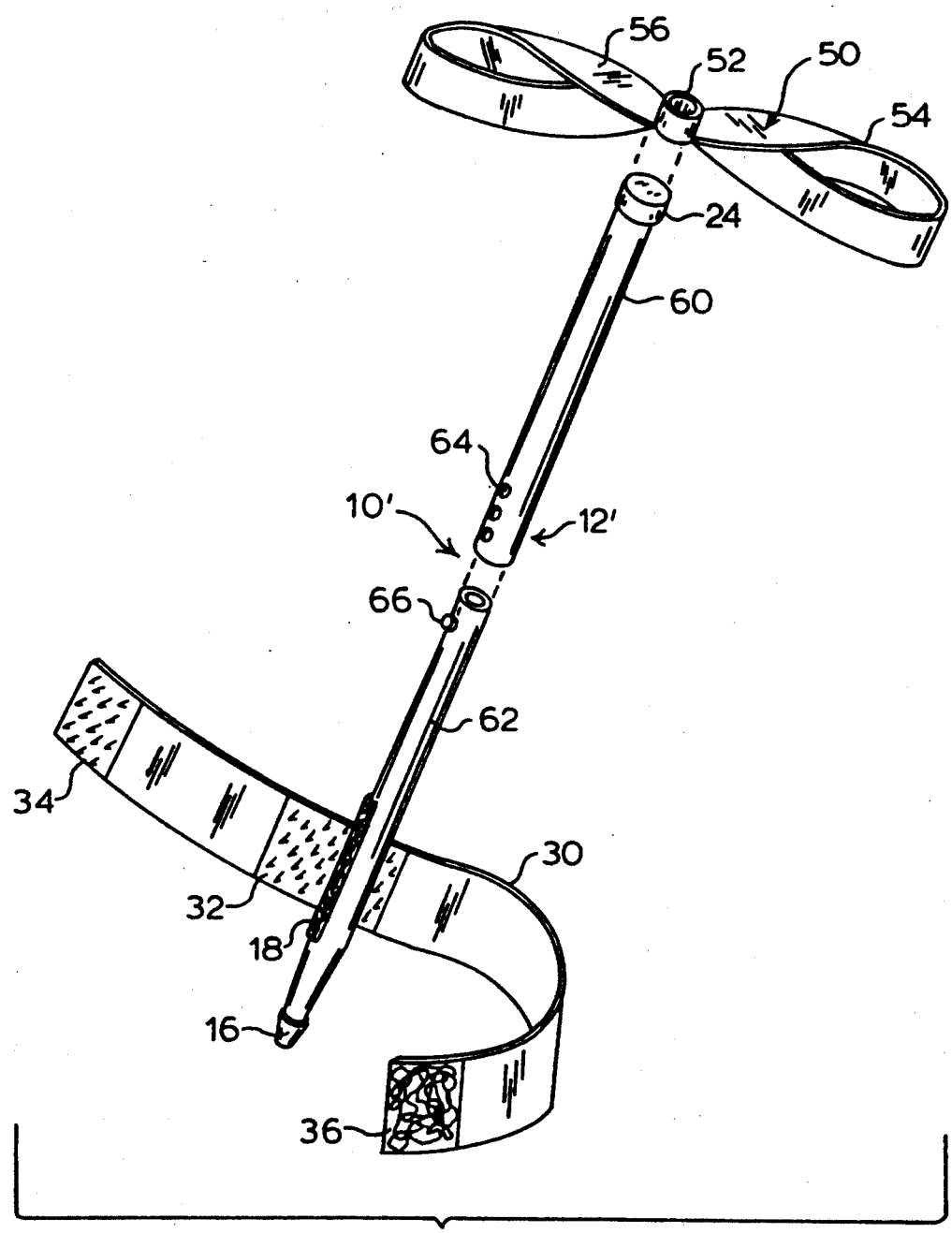
FIG. 3 is an exploded view of the posture training and correcting device of the invention incorporating an adjustable rod portion and optional shoulder strap and being shown without a head strap.

The present invention comprises a posture training and correcting device shown generally according to a first embodiment in FIGS. 1 through 5. FIGS. 3 and 4 illustrate a second embodiment whose components may be incorporated into the first embodiment. FIG. 5 illustrates another use for rod employed in either embodiment of the device for encouraging good posture.

First, referring to FIGS. 1 and 2 and the first embodiment, posture training and correcting device 10 comprises a rigid or substantially rigid rod 12, abdominal belt 30 and head strap 40. Although the measurements and configuration of rod 12 may vary, rod 12 in a preferred form is generally cylindrical, approximately 36 inches long, and approximately 3 inches in circumference and may be formed of metal, wood, molded plastic or the like. Rod 12 has a top or upper end 22 and a tapered bottom or lower end 14 opposite top end 22. End 22 mounts a resilient, molded top cap 24 and end 14 mounts a resilient, molded tapered cap 16, respectively, to protect the wearer from any rough edges on rod 12. Tapered end 14 generally fits against the base of spine of the wearer, centered from the crease in the buttock upward over the lumbar and thoracic cervical area of the spine.

Rod 12 may be secured to the wearer's body at two or three locations: the abdominal area, the head, and the shoulders. The manner in which rod 12 attaches to the wearer's body permits the wearer to maintain normal activity and does not require that the wearer hold the device in place. The first embodiment is illustrated as having abdominal belt 30 and head strap 40 (shown generally in FIGS. 1 and 2). Abdominal belt 30 is preferably constructed of an elasticized material to allow flexibility and comfort for the wearer, and is preferably at least 2 inches wide and more preferably approximately 4 inches wide. Abdominal belt 30 has a first end 34 and a second end 36 and generally encloses and presses rod 12 against the spine of the wearer at the abdominal area. Ends 34 and 36 meet and interlock to form closure 38 (FIG. 2). Abdominal belt 30 includes in a central portion an attachment means 32 which attaches to belt attachment 18 on rod 12. Belt attachment 18 may be a strip of hook and loop closure material, such as VELCRO TM material, beginning approximately 5 inches from tapered end 14 and extending approximately 6 inches along rod 12. Attachment means 32 may also be of hook and loop closure material located at the center of the length of belt 30. Belt attachment 18 permits belt 30 to be attached at various positions on rod 12 so that belt 30 can surround the abdominal areas of wearers having different torso lengths. Attachment means 32 may also be formed as a loop (not shown) in abdominal belt 30 which snugly fits and is axially adjustable on rod 12 by sliding abdominal strap 30 along rod 12.

First end 34 and second end 36 of belt 30 interlock at a closure 38 to permit abdominal belt 30 to adjustably close around the wearer's abdominal area, preferably in front of the wearer so that the wearer has easy access to closure 38 (shown in FIG. 2). Closure 38 may also comprise hook and loop material such as VELCRO TM material secured respectively to each end 34 and 36 of belt 30. When in use, abdominal belt 30 holds rod 12 securely to the wearer's spine and exerts pressure on the abdominal area of the wearer, causing the wearer to contract the abdominal muscles and press the spine to rod 12, thus encouraging correct posture.

Head strap 40, shown in FIGS. 1 and 2, is attached to rod 12 near top end 22 of rod 12 and encircles the wearer's head at the forehead area. Head strap 40 is preferably constructed of elasticized material of approximately 1½ inches in width to allow flexibility and comfort for the user. The elasticized material used for head strap 40 may have more elasticity than abdominal strap 30 to permit a comfortable fit around the wearer's head. The tension of head strap 40 should allow for the pulling of the wearer's head toward rod 12, while at the same time allowing for the lateral and forward mobility of the wearer's head. Head strap 40 has in a central portion an attachment means 42 which permits head strap 40 to attach to rod 12 and is preferably made by forming a snugly fitting loop in head strap 40 (shown in FIG. 1) at approximately the center of the length of head strap 40. Because tapered end 14 must be placed at the base of the spine area of the wearer, the position of head strap 40 on rod 12 is adjusted and located to fit each wearer. Therefore, a significant flexibility of the vertical placement of head strap 40 on rod 12 must be permitted to accommodate wearers having various heights. First end 44 and second end 46 of head strap 40 meet to form a closure 48, preferably in front of the wearer's forehead (shown in FIG. 2). Closure 48 may comprise interlocking hook and loop material such as the previously mentioned VELCRO TM material secured to the ends 44, 46 of head strap 40 to permit easy and adjustable connection of first end 44 and second end 46 around the wearer's head.

When head strap 40 and abdominal belt 30 are secured around the wearer, the wearer's lumbar, thoracic spine and head are urged toward rod 12. In this position, the wearer's relevant body parts are in correct alignment for correct posture. While the body parts are in correct alignment, the relevant muscles are contracted. After use of the device for a period of time, the wearer will subconsciously contract those same muscles (the abdomen muscles, the upper thoracic spinal muscles and the rib elevator muscles) to achieve correct posture.

The second embodiment also comprises a shoulder strap 50 comprising right shoulder loop 54 and left shoulder hoop 56, shown in FIGS. 3 and 4. Shoulder strap 50 is preferably constructed of an elasticized material approximately 1 inch in width. As best seen in FIG. 4, shoulder strap 50 stabilizes rod 12' in the center of the wearer's back over the spine. The slight pull of shoulder strap 50 on the wearer's shoulders encourages drooped shoulders to become straightened. Shoulder strap 50 attaches to rod 12' by the centrally located attachment means 52. Attachment means 52 permits the adjustable vertical or axial placement of shoulder strap 50 on rod 12' to accommodate wearers having different shoulder heights, and is illustrated as comprising a snugly fitting loop 52 which is slidable on rod 12', shown in FIG. 3. It is to be noted that the entire shoulder strap 50 may be sewn from a single strip of elastic material. Also to be noted is that the caps 16, 24, abdominal belt 30 and head strap 40 of the first embodiment may be employed with the second embodiment and secured as in the first embodiment as illustrated in FIG. 3.

The versatility of use of rod 12 of the first embodiment as a posture device is illustrated in FIG. 5. In this alternate method, the wearer places rod 12 horizontally behind his back at the waist, holding rod 12 in place by hooking his arms around rod 12 so that rod 12 extends through both arms at the inner elbows. This alternate use corrects poor spine position and encourages upright posture.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. A postural training and corrective device which provides a simple method of analyzing and training a person to recognize and correct faulty posture, comprising the elements of:
   (a) a straight rigid rod tapered at the end, beginning at the lower back over the sacrum, extending vertically up over the lumbar and thoracic spine, ending at the top of the person's head;
   (b) a strong elastic band attached on the rod for adjustable axial positioning over the lumbo-sacral area, reaching around the abdomen and fastening as a means of holding said rod firmly against the spine, exerting pressure on the abdomen, yet allowing forward, backward and lateral movement of the spine;
   (c) a head band of weaker elastic attached for adjustable axial positioning on said rod by elastic attachment means, extending forward and encircling the forehead area providing a means for pulling the head gently toward said rod while allowing natural movement of the head;
   (d) a band of elastic attached for adjustable axial positioning on said rod at the upper thoracic spine, extending laterally to form two shoulder loops, one fitting around the right shoulder and one fitting around the left shoulder, providing a means for holding said rod centered over the thoracic spine and as a means of reminding the wearer to square up drooping shoulders;
wherein when all of said elements are worn in position, wearer's body is urged into correct posture.

2. A posture training and correcting device as claimed in claim 1 wherein said device includes interlocking hook-and-loop fastening means mounted on selected portions of said rod, belt and headband to permit said axial positioning.

3. A posture training and correcting device as claimed in claim 1 wherein selected central portions of said elastic belts are formed as a loop adapted to snugly engage and slide on said rod to permit said axial positioning.

4. A simple method for training a human to recognize and correct faulty posture by stimulating the person to contract relaxed muscles which have produced poor posture, comprising the steps of:
   (a) positioning a straight rigid rod tapered at the end, beginning at the lower back over the sacrum, extending vertically up over the lumbar and thoracic spine, ending at the top of the person's head;
   (b) positioning a strong elastic band attached to the rod for adjustable axial positioning over the lumbo-sacral area, reaching around the abdomen and fastening as a means of holding said rod firmly against the spine, exerting pressure on the abdomen, yet allowing forward, backward and lateral movement of the spine;
   (c) positioning a head band of weaker elastic attached for adjustable axial positioning to said rod by elastic attachment means, extending forward and encircling the forehead area providing a means for pulling the head gently toward said rod while allowing natural movement of the head, thereby producing a stage of postural correction;
   (d) positioning two shoulder loops of elastic, one loop around the right shoulder and one loop around the left shoulder and the loops being attached on said rod for adjustable axial positioning at the upper thoracic spine, providing a means for holding said rod centered over the thoracic spine and as a means of reminding the wearer to square up drooping shoulders, thereby producing a further state of postural correction.

* * * * *